United States Patent
Mulvey

(10) Patent No.: US 8,573,353 B2
(45) Date of Patent: Nov. 5, 2013

(54) LONG-WEARING DEEP-INSERTION EAR TIP

(75) Inventor: David B. Mulvey, San Diego, CA (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/335,313

(22) Filed: Dec. 22, 2011

(65) Prior Publication Data
US 2013/0161119 A1    Jun. 27, 2013

(51) Int. Cl.
*H04R 25/02* (2006.01)

(52) U.S. Cl.
USPC .......................................... 181/135; 181/130

(58) Field of Classification Search
USPC .......................... 181/129, 130, 135; 128/864
See application file for complete search history.

(56) References Cited

U.S. PATENT DOCUMENTS

| | | | | |
|---|---|---|---|---|
| 1,830,198 A | * | 11/1931 | French | 181/135 |
| 3,303,902 A | * | 2/1967 | Knott | 181/135 |
| 3,934,100 A | * | 1/1976 | Harada | 181/135 |
| 5,002,151 A | * | 3/1991 | Oliveira et al. | 181/130 |
| 6,006,857 A | * | 12/1999 | Leight et al. | 181/135 |
| 7,236,605 B2 | * | 6/2007 | Oliveira et al. | 381/328 |
| D599,907 S | | 9/2009 | Mulvey et al. | |
| 7,600,604 B2 | * | 10/2009 | Babcock et al. | 181/130 |
| 7,837,005 B2 | * | 11/2010 | Killion | 181/129 |
| 2010/0300461 A1 | | 12/2010 | Glider et al. | |

FOREIGN PATENT DOCUMENTS

WO    2010135688 A1    11/2010

\* cited by examiner

*Primary Examiner* — Jeremy Luks
(74) *Attorney, Agent, or Firm* — Kristin Jordan Harkins; Conley Rose P.C.

(57) ABSTRACT

Embodiments typically relate to ear tips for sound transmission devices, designed to fit snuggly in the user's ear canal and block external noise from the environment while being sufficiently comfortable for long-wearing and/or deep insertion. Embodiments may comprise a stem and a foam body, with the hollow stem lying on the centerline of the foam body. The foam body may comprise a concave opening in its nose, a rear extension flange projecting rearward to extend its length without significantly impacting perceived comfort, and/or a plurality of indentations about the periphery of the nose of the foam body. The foam body may be formed of polyurethane foam, and the stem may be formed of elastomeric polyurethane.

19 Claims, 4 Drawing Sheets

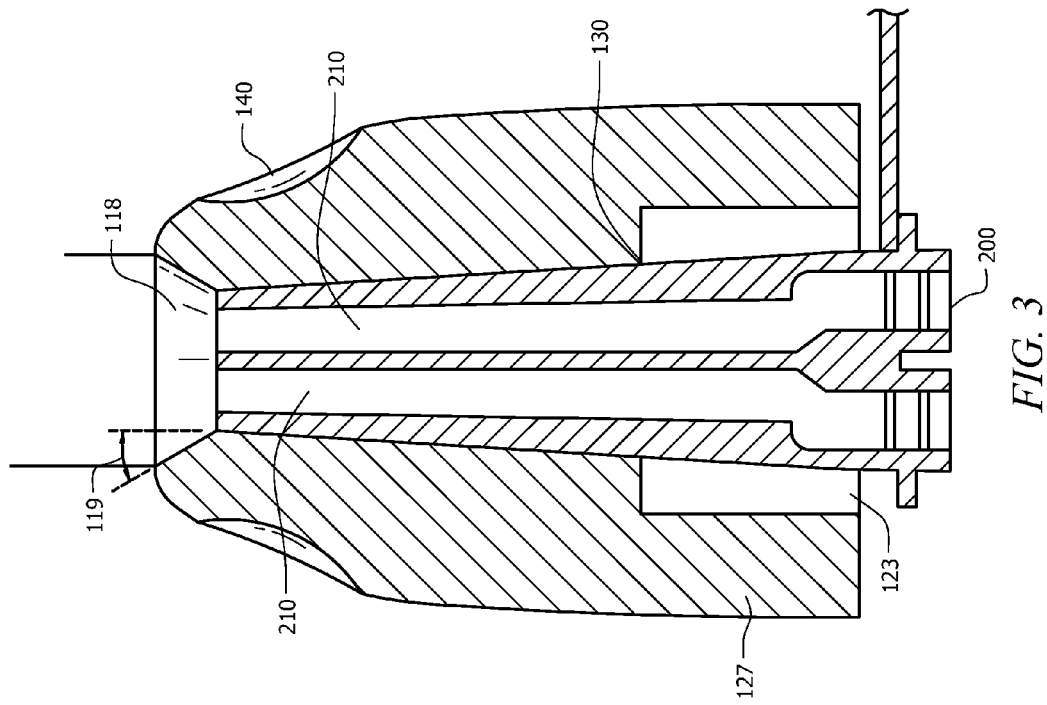
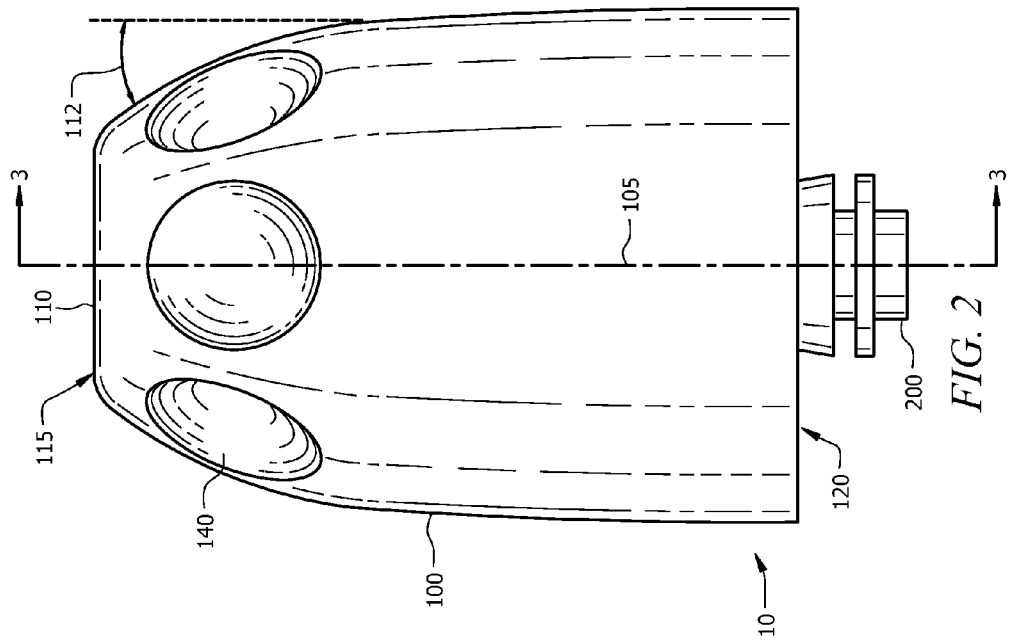

LONG-WEARING DEEP-INSERTION EAR TIP

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

FIELD

Embodiments may relate generally to ear tips for ear buds and other electronic sound transmission devices (typically for directing sound into a user's ear), and more specifically to foam ear tips designed to provide a good seal while also being sufficiently comfortable to be worn for long durations.

BACKGROUND

For some uses, standard ear tips either will not provide sufficient seal to block out external noise that might interfere with sound quality in the user's ear and/or to provide noise reduction to protect the user from external sound that could potentially cause hearing damage, or will not be sufficiently comfortable to be worn for long periods of time. For example, if the ear tips are used with an in-ear communication device for use during working hours, then the user might need the ear tip to provide an effective seal against environmental noise (as might be required by OSHA regulation, for example) and to be sufficiently comfortable to be worn during an entire work shift. The ear tips of the present embodiments are designed to provide a comfortable, long-wearing seal for a user's ear. This can be especially important for deep-insertion ear tips, such as those needed for the QuietPro device made and sold by Nacre AS. Such deep-insertion sound devices interact with especially sensitive portions of the ear canal, making comfort issues particularly important. This is especially true since such devices are often used for extended periods, with users leaving the ear tips in place for many hours (often 8 hours or more). And the QuietPro device, for example, also requires an effective seal despite these comfort concerns, since it checks for seal effectiveness in order to allow for effective communication even in loud noise environments.

Typically, comfort design constraints conflict with the quality of the seal. In other words, for most standard ear tips a more comfortable ear tip would result in a decrease in seal effectiveness. Applicant has designed new ear tips, however, which provide seal effectiveness while also being sufficiently comfortable to allow for long-wearing usage.

SUMMARY

Aspects of the disclosure may include embodiments of an EarTip comprising one or more of the following elements and/or features in any combination: a foam body; and a stem comprising one or more sound tubes therethrough; wherein: the foam body comprises a front portion having a front and a rear portion having a rear; the front portion of the foam body comprises a nose angled to improve insertion; the foam body comprises a centerline and a through passage located on the centerline; the stem is located along the centerline in the passage; a portion of the passage is approximately the same width as the stem; a front portion of the passage forms a concave opening in the nose of the foam body; the stem extends from the concave opening rearward along the centerline of the foam body past the rear end of the foam body; a rear portion of the passage widens to form a hollowed-out annular space about the stem so that the rear portion of the foam body comprises an integrated rear extension flange encompassing the annular space and the stem; a plurality of indentations are located on a periphery of the nose of the foam body and are evenly space about the periphery; the stem is attached to the foam body; the foam body is made of polyurethane foam; and the stem is made of elastomeric polyurethane. The foam body may have a length of approximately 0.69 inches, and the rear extension flange may have a length of approximately 0.2 inches and a thickness ranging from approximately 0.08 to 0.1 inches. The nose may have an angle of attack ranging from approximately 16 degrees to approximately 27 degrees, the concave opening in the nose may have a concave angle of approximately 25-30 degrees, and there may be between 4 and 6 indentations, which may be semi-spherical in shape and may each have a diameter ranging from approximately 0.165 to approximately 0.172 inches and/or a depth ranging from approximately 0.005 to approximately 0.025 inches. In some embodiments the stem may be stiffer than the foam body and may have a durometer (hardness) range between about 65 and about 85 Shore A. The stem may be attached to the foam body by a solvent-based adhesive. In some embodiments, the Ear-Tip may be an ear tip for a sound transmission device.

BRIEF DESCRIPTION OF THE DRAWINGS

For a more complete understanding of the present disclosure, and for further details and advantages thereof, reference is now made to the accompanying drawings, in which:

FIG. 2 shows a side elevation view of the ear tip of FIG. 1;

FIG. 3 shows a cross-sectional view of the ear tip of FIG. 1 taken along plane A-A;

DETAILED DESCRIPTION

Figure 1:
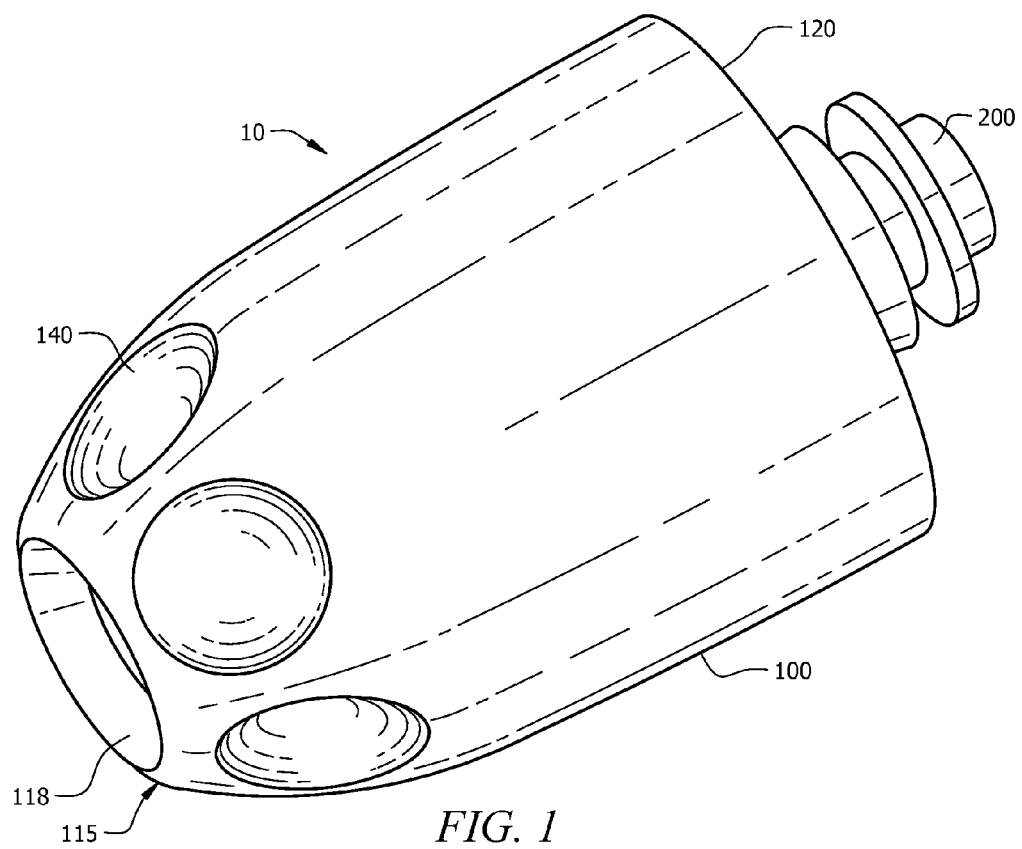
FIG. 1 shows a perspective view of an embodiment of an ear tip
Figure 4:
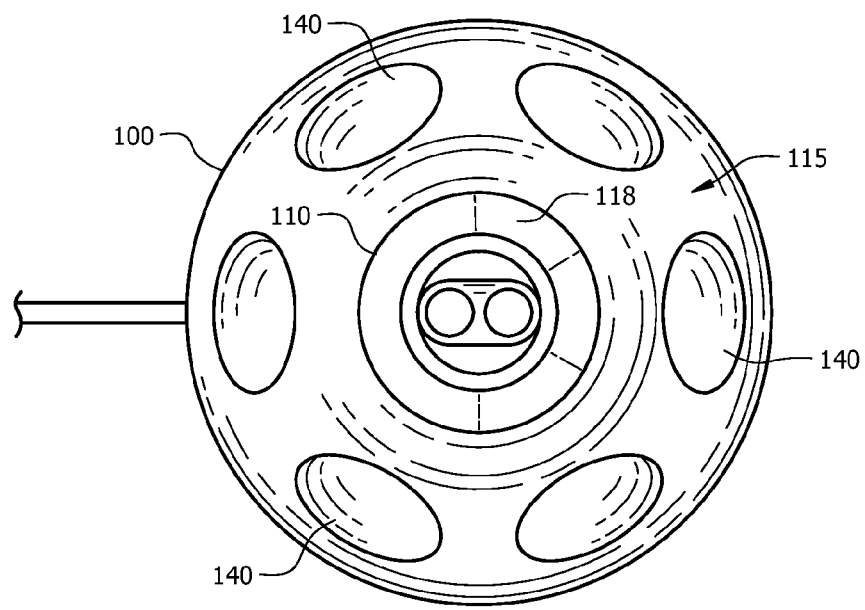
FIG. 4 shows a front elevation view of the ear tip of FIG. 1.
Figure 5:
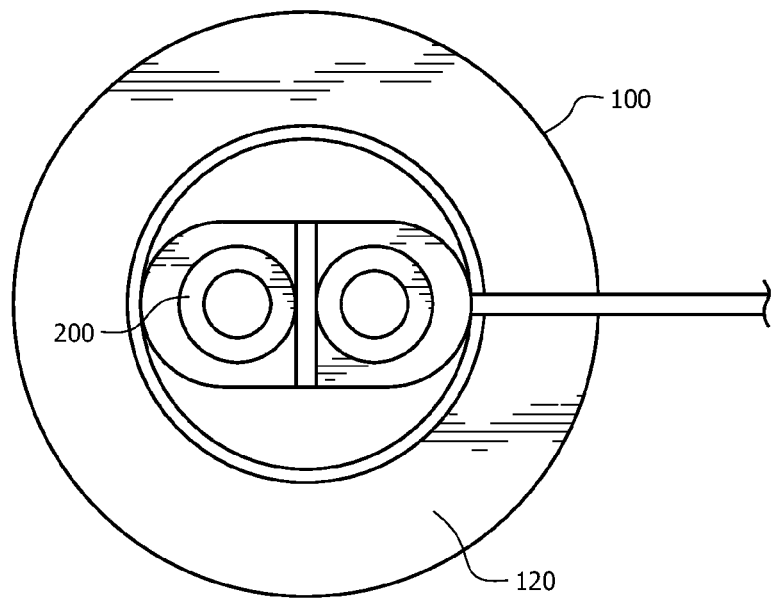
FIG. 5 shows a rear elevation view of the ear tip of FIG. 1.

The following brief definition of terms shall apply throughout the application:

The term "EarTip" generally refers to either an ear tip for use on a sound transmission device (such as an earbud for a communication headset, a hearing aid, or a portable music device, by way of non-exclusive example), to an earplug for protecting the user's hearing, or to any device comprising such ear tip or earplug elements, with the EarTip typically comprising a resilient portion designed to fit snugly in a user's ear canal; while this disclosure typically describes embodiments directed to ear tips, it should be understood that the disclosure is broad enough to include any sort of EarTip;

The term "foam" generally refers to a foam material with resilient recovery properties; foam materials may be low resilient and have slow recovery properties, such that if the foam is compressed and then released, the foam returns back towards its original uncompressed state over a period of time (typically greater than 10 seconds but less than 30 minutes, for example); or foam materials may be resilient and have moderate to fast recovery properties, such that they do not take a long-term set but return back towards the original uncompressed state fairly quickly (typically less than 10 seconds, for example); foam materials may be viscoelastic, and one example of such a viscoelastic foam plastic might be latex-modified polyurethane foam;

The term "sound transmission device" generally refers to any device for transmitting sound into a user's ear canal from an outside source, and by way of nonexclusive example may include personal music devices (such as an IPod.™), a communication headset or earpiece, or a hearing aid;

The terms "front" and "rear" are used as relative descriptions of the opposing ends of an EarTip, with "front" typically describing the end that is directed towards and closest to the ear drum when the EarTip is inserted in a user's ear canal, and "rear" typically describing the end that is directed outward, away from, and furthest from the ear drum;

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a nonexclusive example;

The terms "about" or approximately" or the like, when used with a number, may mean that specific number, or alternatively, a range in proximity to the specific number, as understood by persons of skill in the art field; and If the specification states a component or feature "may," "can," "could," "should," "preferably," "possibly," "typically," "optionally," "for example," or "might" (or other such language) be included or have a characteristic, that particular component or feature is not required to be included or to have the characteristic. Such component or feature may be optionally included in some embodiments, or it may be excluded.

FIG. 1 shows a perspective view of an embodiment of an ear tip 10 with an outer shape to fit securely within a user's ear canal in order to effectively seal the ear canal against passage of external sound from the external noise environment. FIGS. 2-5 show additional views of the ear tip 10 of FIG. 1, with FIG. 3 for example showing a cross-sectional view of the ear tip of FIG. 1. The ear tip 10 embodiment of FIG. 1 includes a foam body 100 having a through passage 130 located on its longitudinal centerline 105, and a stem 200 located within the foam body 100 along the centerline 105 (such that the stem lies within at least a portion of the passage 130). The foam body 100 may be formed of any suitable foam material, and in the embodiment of FIG. 1 the foam body 100 is typically formed of polyurethane foam. The foam of the foam body 100 of FIG. 1 typically has a density range of about 1.70e-05 to 2.52e-05 gram per cubic millimeter (where the well-known mathematical constant "e" is approximately 2.71828, for example). The stem 200 is typically made of a material more rigid than that used for the foam body, but is nevertheless more flexible and/or pliable than a standard stem for a sound transmission device (since this may improve comfort, improve insertion, and/or provide a better fit by allowing the stem to better conform to the user's ear canal). The flexibility of the stem may generally be a function of its hardness in conjunction with its geometric parameters (such as width of walls and shape, for example). In the embodiment of FIG. 1, the stem 200 may have a hardness ranging from about 65 to about 85 Shore A and/or be formed of elastomeric polyurethane. In alternative embodiments, the stem might be formed of an alloy with TPE silicon. The stem in the embodiment of FIG. 1 may have a width that is substantially the same as at least a portion of the through passage 130 in the foam body (such that the stem 200 typically fits snuggly within at least a portion of the passage 130). Typically, the stem 200 is securely attached to the foam body 100. While the attachment may be by means of glue or some other adhesive, in FIG. 1 a solvent-based adhesive may be used instead of glue, since the solvent tends to be less stiff than glue and may therefore improve comfort.

In FIG. 1, the foam body 100 typically may have a snubnosed bullet shape, often having approximately circular cross-sections that widen from front to rear. The foam body 100 of FIG. 1 includes a nose 115 located at the front 110 of the ear tip 10 and being shaped with an angle of attack 112 that facilitates insertion into a user's ear. In the embodiment of FIG. 1, for example, the angle of attack 112 might range from about 16 degrees to about 27 degrees. The front 110 of the nose 115 of FIG. 2 is typically flat in shape, with a width of about 0.16-0.23 inches. The width of the rear 120 of the foam body 100 of FIG. 2 is typically about 0.41-0.57 inches. The nose 115 of FIG. 1 may include a plurality of indentations (or scallops) 140 spaced evenly about its periphery. Typically the indentations 140 are semi-spherical in shape and have a diameter of between about 0.165 and about 0.172 inches and a maximum depth of between about 0.005 and about 0.025 inches. The term "semi-spherical" is intended to include shapes other than merely true spheres, including by way of example ovaloids and elliptical shapes. And while the indentations of FIG. 1 may be approximately semi-spherical in shape, other shapes may be used to achieve functionality and are included herein. The embodiment of FIG. 1 typically has between 4 and 6 indentation 140 in the nose 115, each of which may be located approximately 0.05 inches from the front 110 of the ear tip 10. This scalloping of the nose 115 with a pattern of indentations 140 may improve insertion characteristics.

The nose 115 of FIG. 1 also includes a concave opening 118 in the front 110 that opens into the through passage 130. Stated another way, the front of the through passage 130 may widen from about the width of the front of the stem 200 (and located longitudinally from the front of the stem 200 forward to the front of the ear tip 10) to form a concave opening 118. The concave opening 118 typically has a concave angle 119 ranging from between about 25-30 degrees and/or a depth of about 0.07 inches (down to the front of the stem). The width of the front of the concave opening 118 of FIG. 1 may range from about 0.16 to about 0.23 inches, while the width of the rear of the concave opening is typically equal to the width of the front of the stem 200. The concave opening 118 may be more clearly seen in the cross-sectional view of FIG. 3.

The rear portion of the foam body 100 is undercut to provide an open rear annular space 123 about the rear of the stem 200. In effect, the rear of the foam body 100 includes an integral rear flange (or skirt) 127 that extends out rearward from the main body of the foam body 100. The rear extension flange or skirt 127 includes a periphery that encompasses the rear of the stem 200 and the rear annular space 123 (so that the rear of the stem 200 is inset radially inward from the rear of the foam body 100, forming the rear annular space 123 between the stem 200 and the rear extension flange 127 of the foam body). The rear annular space 123 of FIG. 3 typically has width (between the stem 200 and the extension flange 127) sufficient to provide for inward deflection of the rear extension flange 127 for comfort, and encircles the stem 200. By allowing inward deflection, the seal may be improved by extension of the length of the ear tip without significantly impacting comfort. In the embodiment of FIG. 3, the rear extension flange may range in thickness from about 0.08-0.10 inches, and may have a length of about 0.20 inches. The maximum length of the rear extension flange or skirt 127 may typically be determined by the processing limits for molding the ear tips. By incorporating the rear extension flange or skirt 127, the length of the ear tip 10 may be extended up to about 0.690 inches (which is about a 75% increase over standard tip length—typically 0.42+/−0.10 inches) without substantially increasing perceived pressure in the user's ear canal. The ear tip foam body 100 of FIG. 1 has a length of about 0.69 inches. In this way, the rear extension flange 127 may improve the seal for sound blocking without significantly impacting comfort for long-term wear.

The stem 200 of FIG. 3 comprises two hollow sound tubes 210 running longitudinally, with front ends that open into the concave opening 118 in order to project sound out of the ear tip 10 and into a user's ear canal (and/or possibly in other embodiments, to detect sound from within the ear canal and/or other functions requiring access to the ear canal through the sound seal provided by the foam body). Typically, the front of the sound tubes 210 will not extend into the concave opening 118. Each sound tube 210 aperture in FIG. 3 widens from the rear of the sound tube 210 towards the front of the sound tube, with the walls of the sound tube 210 being thicker towards the rear and thinner towards the front. The thickness variation of the walls of the sound tubes 210 may also result in the stem 200 being more flexible towards its front tip. The stem 200 may have a flattened shape. So typically the stem 200 of FIG. 3 may have an oval cross-section with two identical sound tubes 210 having approximately circular cross-section being joined into an integral unit, and with the stem 200 being wider at its rear than at its front. The stem 200 may have a raised ridge on at least its two flatter sides, serving as a stop upon which the foam body may rest (such that the rear portion of the stem 200 behind the raised ridges would be the portion of the stem encompassed by the rear annular space 123, and the front portion of the stem in front of the raised ridges would be encompassed by, in contact with, and/or bonded to the foam body). In some embodiments, a single raised ridge encompasses the periphery of the stem 200.

So the foam body 100 of FIG. 3 has a through passage 130 with a wider front portion forming a concave opening 118 in the nose 115 of the foam body 100, and a wider rear portion forming a hollowed-out annular space 123 about the stem 200 so that the rear portion of the foam body 100 is spaced away from the stem 200 and forms a rear extension flange 127 with a periphery encompassing the stem 200 and the rear annular space 123. The central portion of the through passage 130 in FIG. 3 is approximately the same width as the stem 200, with the stem 200 typically being securely attached to the foam body 100 at this central portion. Thus, the stem of FIG. 3 extends from about the rear of the concave opening 118 (such that the front end of the stem 200 is inset from the front 110 of the foam body) rearward and out beyond the rear 120 of the foam body 100.

One or more of the features described above with respect to the embodiment of FIG. 1 may provide for better insertion, improved pliability, improved roll-down, improved comfort, effective sound seal, improved long-wearing capabilities, better deep insertion characteristics, and/or a better balance of one or more of these factors, such that the ear tips of FIG. 1 may be particularly effective for use with sound transmission devices for use in deep-insertion and/or long-wearing scenarios. Thus, the ear tips of FIG. 1 may be particularly useful for a device such as the QuietPro by Nacre AS. For further details about such sound transmission devices, please consult U.S. Pat. No. 6,728,385 for example, which is hereby incorporated by reference for some embodiments herein to the extent that it is not inconsistent with and/or does not contradict information presented directly in the present disclosure.

Figure 6:
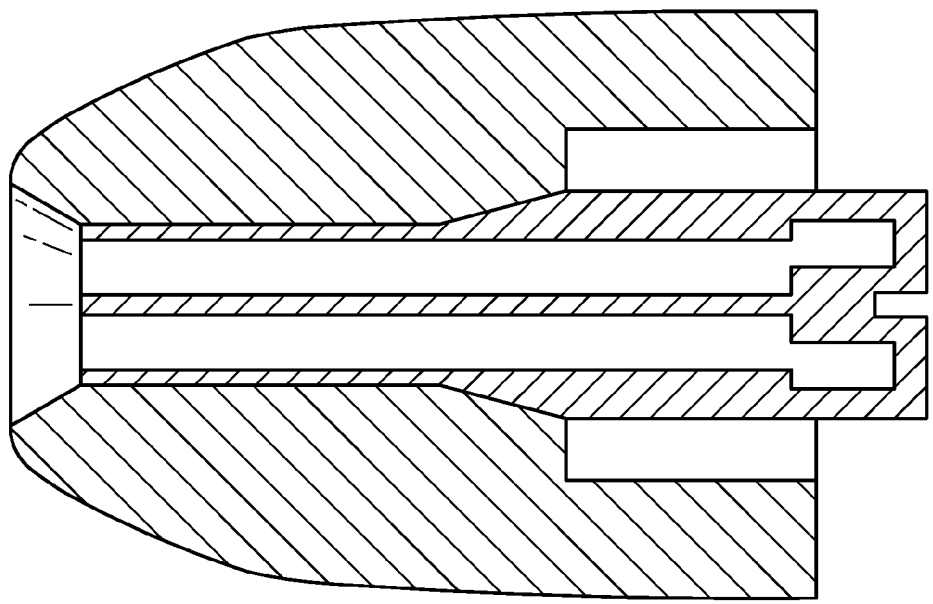
FIG. 6 shows a cross-section view of another embodiment of an ear tip having concave opening in the nose of the foam body and a plurality of indentations about the periphery of the nose of the foam body.
Figure 7:
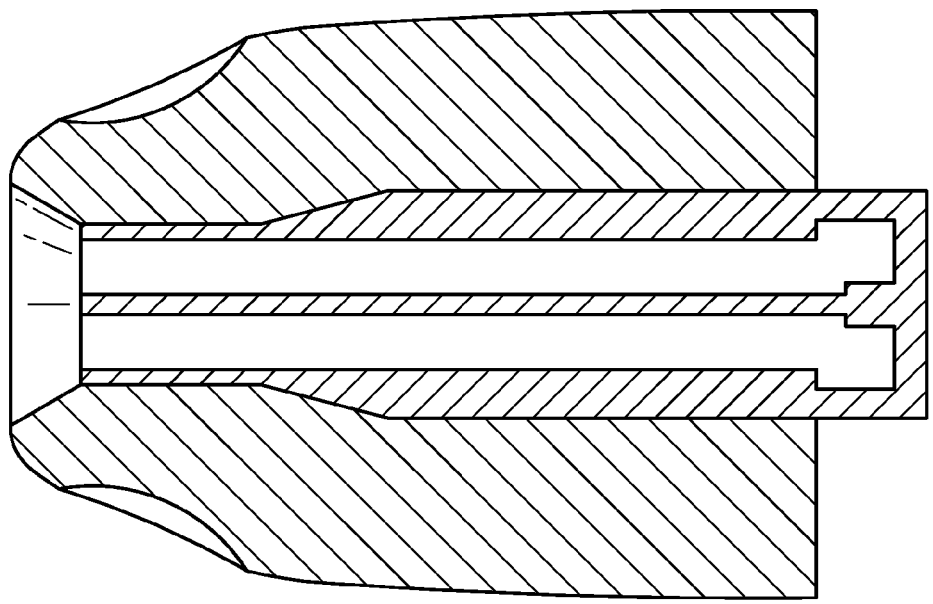
FIG. 7 shows a cross-section view of yet another embodiment of an ear tip having a concave opening in the nose of the foam body and an integrated extending rear flange with hollowed-out annular space between the foam flange and the stem.

Embodiments may also include or delete any one or more of the elements discussed above. For example, FIG. 6 shows a cross-sectional view of an alternative embodiment that includes a foam body having a concave opening in the nose of the foam body and a plurality of indentations (typically semi-spherical and evenly spaced about the periphery of the nose), without including the rear extension flange discussed above for FIG. 1. FIG. 7 shows a cross-sectional view of yet another embodiment that includes a foam body having a concave opening in its nose and a rear extension flange (resulting in a hollowed-out annular space about the rear portion of the stem), without also having any indentations about the periphery of the nose. Another exemplary embodiment might include a foam body having a plurality of indentations about the nose of the foam body and/or a rear flange extension, without also having a concave opening in the nose. And for example, any of these embodiments might include a flexible stem having a hardness of about 65 to about 85 Shore A, which might be formed of elastomeric polyurethane in some embodiments. Persons of skill should understand that the exemplary embodiments are not limiting, and that various combinations of elements and features are intended to be included within this disclosure.

Applicant also notes that, especially for press-in (non-rolldown) EarTips, surface finish characteristics may be important to improve ease of insertion. Thus, it may be beneficial to provide an even smoother surface than provided by the dense skin of the polyurethane foam discussed in embodiments above, lowering the kinetic coefficient of friction to reduce resistance to insertion. Of course, it is also important that the static coefficient of friction not be reduced too much, so that the earplug will remain securely in place during usage (and will not back out and thus compromise the sound attenuation qualities of the earplug). Surface treatments with lubrication enhancing materials may help. It may also be beneficial to introduce such lubricity materials into the foam itself in the hopes of improving the insertion characteristics of the earplug, although cost factors may come into play. Applicant hereby incorporates by reference U.S. published patent application No. 2010-0300461 entitled "Improved EarTip" filed May 21, 2010 for some embodiments herein to the extent that it is not inconsistent with and/or does not contradict information presented directly in the present disclosure.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of, consisting essentially of, and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

What is claimed is:

1. An ear tip comprising:
a foam body; and
a stem comprising one or more sound tubes therethrough; wherein:
the foam body comprises a front portion having a front and a rear portion having a rear;
the front portion of the foam body comprises a nose angled to improve insertion;
the foam body comprises a centerline and a through passage located on the centerline;
the stem is located along the centerline in the passage;
at least a portion of the passage is approximately the same width as the stem;
a front portion of the passage forms a concave opening in the nose of the foam body;
the stem extends from the concave opening rearward along the centerline of the foam body past the rear end of the foam body;
a rear portion of the passage widens to form a hollowed-out annular space about the stem so that the rear portion of the foam body comprises an integrated unsupported rear extension flange consisting of foam encompassing the annular space and the stem, such that the stem is inset radially inward from the rear extension flange so that no portion of the stem contacts the rear extension flange and the annular space encircles the stem and provides for inward deflection of the rear extension flange during insertion of the ear tip into a user's ear canal;
a plurality of semi-spherical scalloping indentations are located on a periphery of the nose of the foam body and are evenly space about the periphery;
the stem is in contact with at least a portion of the front portion of the foam body and is directly attached to the foam body;
the foam body is made of polyurethane foam; and
the stem is made of elastomeric polyurethane.

2. The ear tip of claim 1 wherein the foam body has a length of approximately 0.69 inches, and the rear extension flange has a length of approximately 0.2 inches and a thickness ranging from approximately 0.08 to 0.1 inches.

3. The ear tip of claim 1 wherein the nose has an angle of attack ranging from approximately 16 degrees to approximately 27 degrees, wherein the concave opening in the nose has a concave angle of approximately 25-30 degrees, and wherein there are between 4 and 6 indentations each having a diameter ranging from approximately 0.165 inches to approximately 0.172 inches and a depth ranging from approximately 0.005 inches to approximately 0.025 inches.

4. The ear tip of claim 1 wherein the stem is stiffer than the foam body and has a durometer range between about 65 and about 85 Shore A; wherein the stem has a smooth outer surface; and wherein the stem is attached to the foam body by a solvent-based adhesive.

5. An ear tip comprising:
a foam body; and
a stem comprising one or more sound tubes therethrough; wherein:
the foam body comprises a front portion having a front and a rear portion having a rear;
the front portion of the foam body comprises a nose angled to improve insertion;
the foam body comprises a centerline and a through passage located on the centerline;
the stem is located along the centerline in the passage;
at least a portion of the passage is approximately the same width as the stem;
a front portion of the passage forms a concave opening in the nose of the foam body;
the stem extends from the concave opening rearward along the centerline of the foam body past the rear end of the foam body;
a rear portion of the passage widens to form a hollowed-out annular space about the stem so that the rear portion of the foam body comprises an integrated rear extension flange encompassing the annular space and the stem, with the stem inset radially inward from the flange so that the rear extension flange is spaced away from the stem and the annular space encircles the stem; and
the stem is in contact with at least a portion of the front, portion of the foam body and is attached to the foam body.

6. The ear tip of claim 5 Wherein the foam body has a length of approximately 0.69 inches, and the rear extension flange has a length of approximately 0.20 inches and a thickness ranging from approximately 0.08 to 0.1 inches.

7. The ear tip of claim 5 wherein the nose has an angle of attack ranging from approximately 16 degrees to approximately 27 degrees, and wherein the concave opening in the nose has a concave angle of approximately 25-30 degrees.

8. The ear tip of claim 5 wherein the foam body is made of polyurethane foam; the stem is made of elastomeric polyurethane; the foam body has a density range between about 1.70e-05 and about 2.52e-05 grams per cubic millimeter; and the stem has a durometer range between about 65 and about 85 Shore A.

9. The ear tip of claim 5 wherein the stem is attached to the foam body by a solvent-based adhesive.

10. The ear tip of claim 7 wherein the foam body is made of polyurethane foam; the stem is made of elastomeric polyurethane; the foam body has a density range between about 1.70e-05 and about 2.52e-05 grams per cubic millimeter; the stem has a durometer range between about 65 and about 85 Shore A; and the stem is attached to the foam body by a solvent-based adhesive.

11. The ear tip of claim 8 wherein a plurality of semi-spherical scalloping indentations are located on a periphery of the nose of the foam body and are evenly space about the periphery.

12. The ear tip of claim 5 wherein the rear extension flange has a length of at least about 0.20 inches.

13. The ear tip of claim 5 wherein the stem has a smooth outer surface.

14. The ear tip of claim 5 wherein the rear extension flange consists of foam, with the foam of the rear extension flange being unsupported and encompassing the annular space which encircles the stem.

15. The ear tip of claim 5 wherein a plurality of scalloping indentations are located on a periphery of the nose of the foam body and are evenly spaced about the periphery.

16. The ear tip of claim 15 wherein the rear extension flange has a length of at least approximately 0.20 inches.

17. The ear tip of claim 16 wherein the foam body has a length of approximately 0.69 inches.

18. The ear tip of claim 16 wherein the rear extension flange has a thickness ranging from approximately 0.08 to 0.1 inches.

19. The ear tip of claim 15 wherein the scalloping indentations are semi-spherical, there are 4-6 scalloping indentations, and each scalloping indentation has a diameter of approximately 0.165-0.172 inches and a depth of approximately 0.005-0.025 inches.

* * * * *